(12) United States Patent
Nazeck et al.

(10) Patent No.: US 8,852,238 B2
(45) Date of Patent: Oct. 7, 2014

(54) IMPLANT SYSTEM AND MINIMALLY INVASIVE METHOD FOR IMMOBILIZING ADJACENT VERTEBRAL BODIES

(75) Inventors: Benjamin M. Nazeck, San Clemente, CA (US); Choll W. Kim, San Diego, CA (US)

(73) Assignee: Seaspine, Inc., Vista, CA (US)

( * ) Notice: Subject to any disclaimer, the term of this patent is extended or adjusted under 35 U.S.C. 154(b) by 0 days.

(21) Appl. No.: 12/995,996

(22) PCT Filed: Jun. 5, 2008

(86) PCT No.: PCT/US2008/007045
§ 371 (c)(1),
(2), (4) Date: Dec. 2, 2010

(87) PCT Pub. No.: WO2009/148419
PCT Pub. Date: Dec. 10, 2009

(65) Prior Publication Data
US 2011/0082505 A1    Apr. 7, 2011

(51) Int. Cl.
*A61B 17/70* (2006.01)
*A61B 19/00* (2006.01)

(52) U.S. Cl.
CPC ......... *A61B 17/7037* (2013.01); *A61B 17/7002* (2013.01); *A61B 17/7085* (2013.01); *A61B 2019/307* (2013.01)
USPC ....................................................... 606/264

(58) Field of Classification Search
USPC ................................. 606/246–279
See application file for complete search history.

(56) References Cited

U.S. PATENT DOCUMENTS

| | | | |
|---|---|---|---|
| 5,782,833 A | 7/1998 | Haider | |
| 6,485,494 B1 | 11/2002 | Haider | |
| 6,530,929 B1 | 3/2003 | Justis et al. | |
| 6,565,567 B1 | 5/2003 | Haider | |
| 7,160,300 B2 * | 1/2007 | Jackson | 606/273 |
| 7,179,261 B2 * | 2/2007 | Sicvol et al. | 606/86 A |
| 7,695,497 B2 | 4/2010 | Cordaro et al. | |
| 7,811,288 B2 * | 10/2010 | Jones et al. | 606/86 A |

(Continued)

OTHER PUBLICATIONS

The United States Patent and Trademark Office; The International Search Report and the Written Opinion of the International Searching Authority, or the Declaration; International Search Report and Written Opinion; Oct. 1, 2008; pp. 1-10; The United States Patent and Trademark Office.

(Continued)

*Primary Examiner* — Ellen C Hammond
*Assistant Examiner* — Stuart S Bray
(74) *Attorney, Agent, or Firm* — Middleton Reutlinger; Robert H. Eichenberger; Chad D. Bruggeman

(57) ABSTRACT

A spinal implant system for use in immobilizing adjacent vertebral bodies in a minimally invasive manner, including a pair of implants having lengths sufficient so that one of the ends extend outside of a patient's body when the implants are installed. Each implant has a pair of opposed elongated posts which in conjunction with an orthogonally arranged support surface define a transverse opening for receiving a stabilizing rod. A cap having upper and lower surfaces is associated with each implant, each cap and its associated post has means for advancing the cap along the posts toward the support surface to lock a stabilizing rod therebetween. The rod is pivotally coupled to one of the caps so that the rod, when pivoted, will extend between the transverse openings in adjacently installed implants.

27 Claims, 13 Drawing Sheets

(56) References Cited

U.S. PATENT DOCUMENTS

| | | | |
|---|---|---|---|
| 7,909,830 B2* | 3/2011 | Frigg et al. | 606/86 A |
| 7,967,821 B2* | 6/2011 | Sicvol et al. | 606/86 A |
| 8,096,996 B2* | 1/2012 | Gutierrez et al. | 606/86 A |
| 8,100,915 B2* | 1/2012 | Jackson | 606/86 A |
| 8,100,951 B2* | 1/2012 | Justis et al. | 606/279 |
| 2005/0085813 A1 | 4/2005 | Spitler et al. | |
| 2005/0131408 A1 | 6/2005 | Sicvol et al. | |
| 2005/0131421 A1 | 6/2005 | Anderson et al. | |
| 2005/0154389 A1* | 7/2005 | Selover et al. | 606/61 |
| 2006/0007445 A1 | 1/2006 | Va Geen | |
| 2006/0122597 A1* | 6/2006 | Jones et al. | 606/61 |
| 2006/0241600 A1 | 10/2006 | Ensign et al. | |
| 2007/0239159 A1* | 10/2007 | Altarac et al. | 606/61 |
| 2008/0140132 A1* | 6/2008 | Perez-Cruet | 606/301 |
| 2011/0230916 A1* | 9/2011 | Richelsoph | 606/264 |

OTHER PUBLICATIONS

Perez-Cruet MJ; Khoo LT; Fessler RG; Quality Medical Publishing, Inc.; 2006; pp. 150-151.

Perez-Cruet MJ; Khoo LT; Fessler RG; An Anatomic Approach to Minimally Invasive Spine Surgery; Quality Medical Publishing, Inc.; 2006; pp. 150-151.

\* cited by examiner

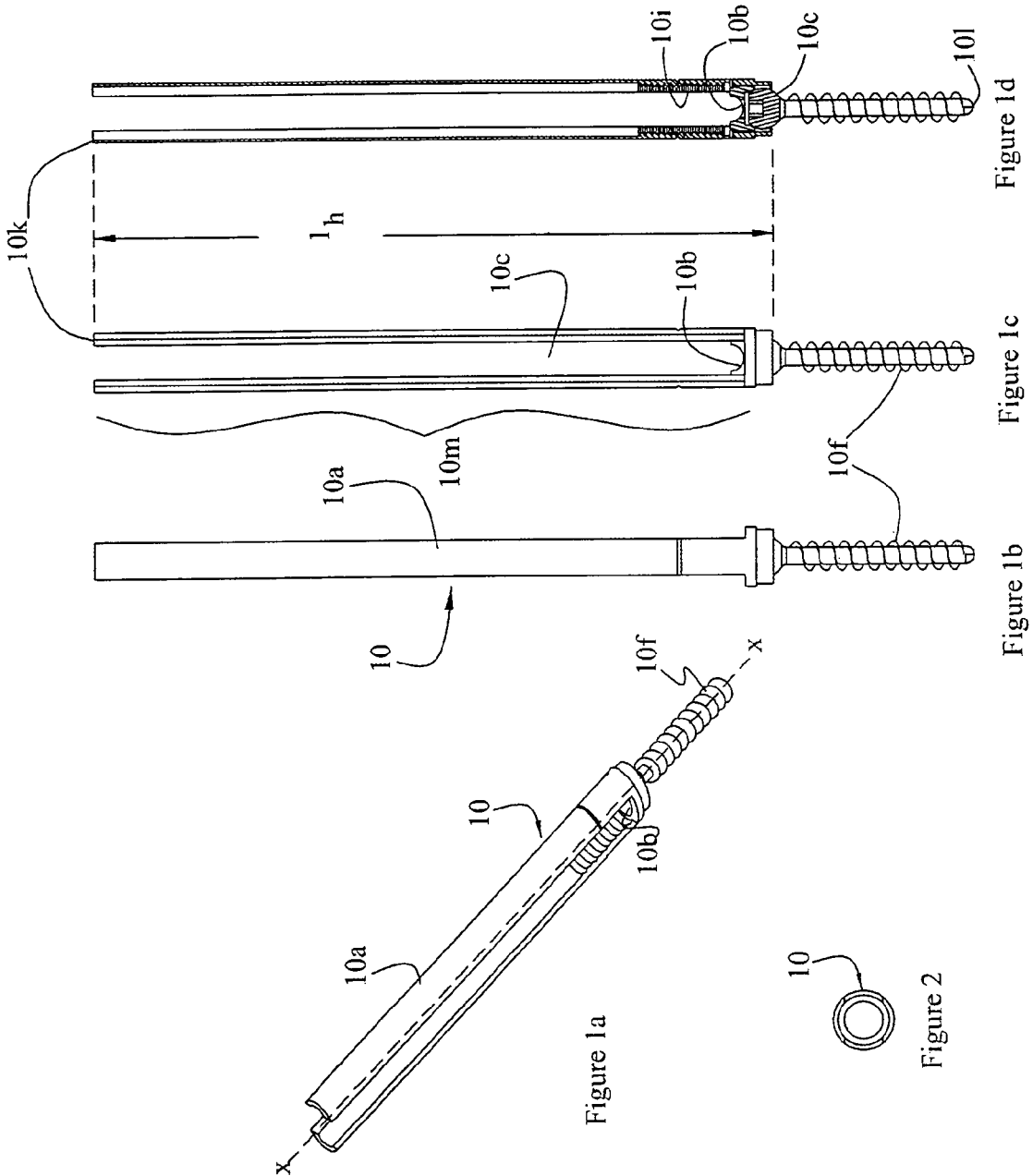

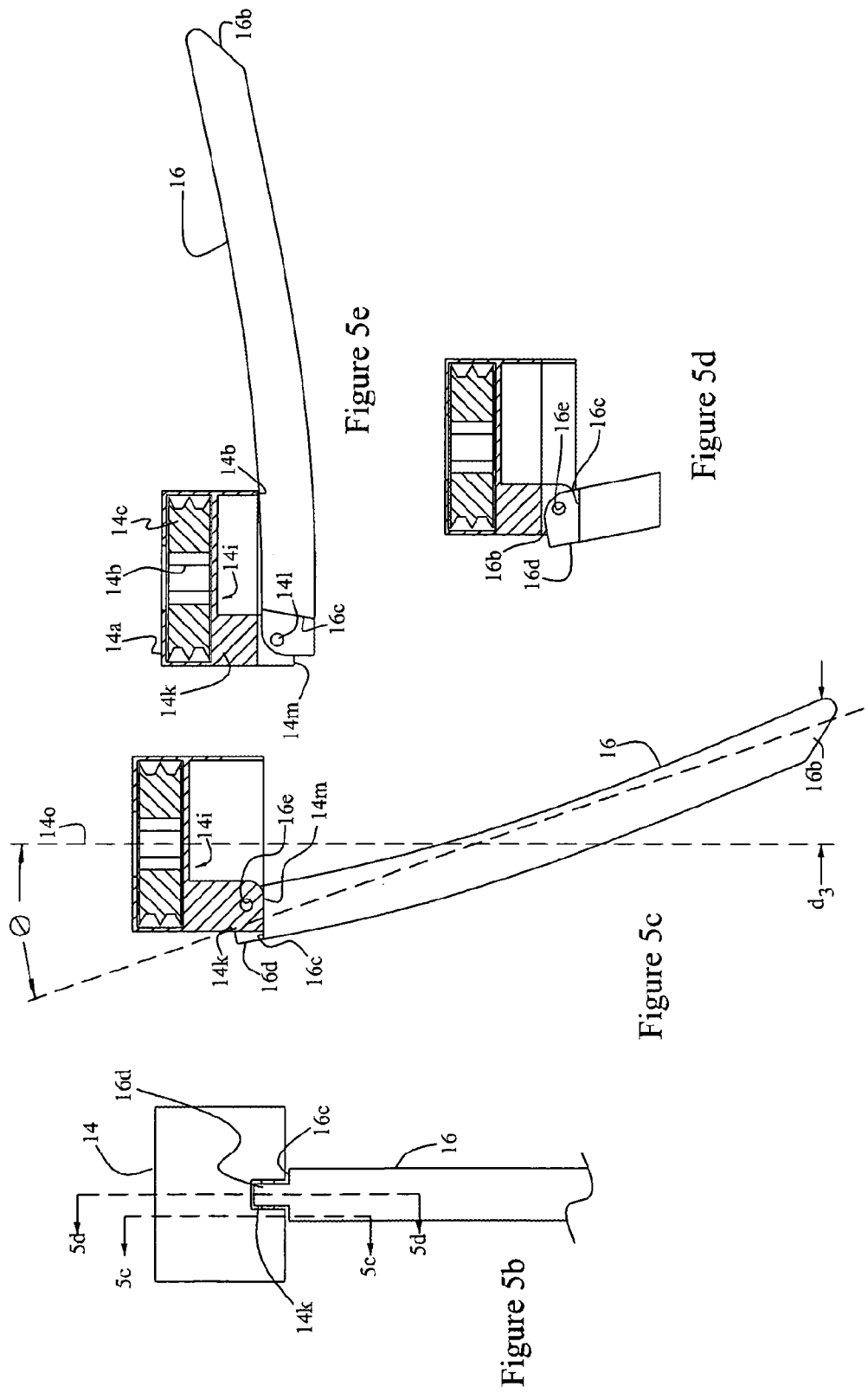

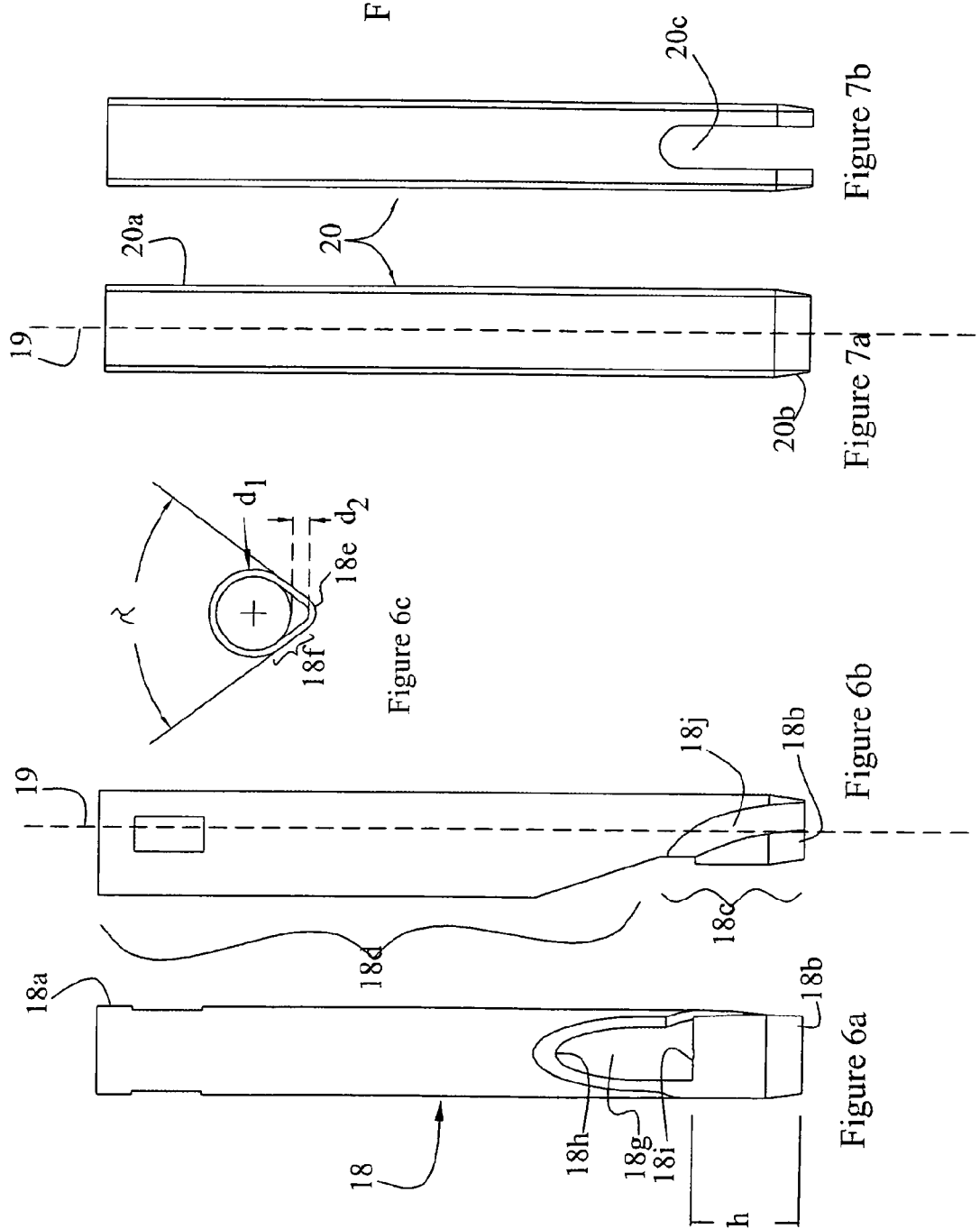

IMPLANT SYSTEM AND MINIMALLY INVASIVE METHOD FOR IMMOBILIZING ADJACENT VERTEBRAL BODIES

TECHNICAL FIELD

The present invention relates to the medical field commonly referred to as Osteosynthesis, i.e., the fusion between segments of the spine and more particularly to an implant system and minimally invasive method for immobilizing the segments preceding the fusion process.

BACKGROUND OF THE INVENTION

Osteosynthesis is achieved by immobilizing separate bone segments and in particular vertebral segments on either side of a failed or damaged disc. When trying to achieve osteosynthesis and specifically fusion between different segments of the spine, one has to provide some type of immobilization. There are various prior art systems and methods which try to achieve this purpose. The different systems involve the placement of implants which typically include pedicle screws threaded into the bone. The implants are then secured to each other by stabilizing or fixation rods.

Traditionally an open large incision is made exceeding the area to receive the implants. Such a large incision involves extensive stripping and/or cutting of musculature from the posterior elements. An implant system successfully used in the traditional approach is described in U.S. Publication No. 2007/0073291 ("'291 publication") which is assigned to the assignee of this application, SeaSpine, Inc. ("SeaSpine"). The contents of the '291 publication are incorporated herein by reference.

Recently the trend has been moving to less invasive techniques and the use of devices accommodating such techniques. A minimally invasive approach attempts to avoid a majority of this muscle stripping and subsequent morbidity by using dilators, to hold open a smaller incision, through which the implants can be inserted. Also, the minimally invasive technique usually relies on the dilators stretching the muscles out of the surgical path rather than cutting them, and the dilators can be placed between natural muscle planes to further avoid muscle damage. As is pointed out in *An Anatomic Approach to Minimally Invasive Spine Surgery*, by Perez-Cruet M J, Khoo L T, Fessler R G, Quality Medical Publishing, Inc. 2006, pg. 150-151:

"Many of the procedures have steep learning curves and require additional training to master, including fellowship training, cadaveric workshops, and animal laboratory study. However, once mastered, these techniques can result in a significant reduction of complications and postoperative pain and discomfort, and allow patients to return to their activities of daily living sooner than standard open, more conventional procedures."

Various prior art minimally invasive techniques and devices for use therewith are discussed in the following U.S. patents and U.S. application publications:

US2005/0131421 ("'421 publication"); US2005/0085813 ("'813 publication"); US2005/0154389 ("'389 publication"); U.S. Pat. No. 6,530,929 ("'929 patent"); US 2006/0122597 ("'597 publication"); U.S. Pat. No. 7,160,300 ("'300 patent"); US2005/0131408 ("'408 publication"); US2006/0241600 ("'600 publication"); and US2006/007445 ("'445 publication").

The above patents/publications disclose different types of implant systems and methods, including the use of a variety of access tubes, to enable a surgeon to install the implants in a relatively less invasive manner. In addition to the installation of the spinal implants, a fixation element, such as a rod, must be securely connected between the installed implants to insure that the distance and orientation of the implants relative to each other remains fixed.

It is the delivery of the spinal fixation rod to the installed implants in a reliable and minimally invasive manner which presents a major challenge. For example, the '421 publication teaches the use of angled guide member positioned at the distal end of one of the access sleeves to transition a loose fixation rod from its lengthwise orientation as it travels down one of the access tubes to a transverse orientation necessary for entering the transverse rod receiving opening in the adjacent implant. Among other shortcomings, it would appear that only a small portion of the rod could be seated in the rod receiving opening in the implant located beneath the guide through which the rod is inserted.

The '455 publication discloses the use of several different tools for positioning a fixation rod into the rod receiving openings in the installed implants. The insertion tools are either designed to penetrate the tissue surrounding the implants to deliver a separate fixed length rod or one positioned outside of the patient's body to deliver an elongated rod through the tissue to the implants with any excess rod being cut off in the surgical area.

The '589 publication, like the '455 publication, discloses the use of an angled guide member positioned at the distal end of an access sleeve to reorient a fixation rod in a transverse direction as it leaves the access sleeve and a rather complicated instrument for seating the reoriented rod in the implants. Such an instrument would not appear to be particularly compatible with a minimally invasive procedure.

The '813 publication discloses the insertion of a fixation rod pivotally mounted on the top of an implant through an access tube. The rotation of the rod serving to screw the pedicle screw of the implant into the underlying bone. The rod is then pivoted out through a slot in the tube and into the rod receiving opening in an adjacent implant with wires extending through the access tube and connected to the proximal end of the rod. The wires are controlled by a manually operated tool arrangement.

The '600 publication discloses a percutaneous pedicle screw assembly in which each pedicle screw is inserted through an access tube and then threaded into the underlying pedicle. Then a housing with a fixation rod pivotally mounted thereto, is assembled over the head of the screw on site via a split ring where the housing is open at the bottom or through a side opening in the housing. The assembly of the housing over the head of an installed pedicle screw deep inside a patient's body would be challenging to a surgeon to say the least. In addition, the method of deployment of the fixation rod from an orientation aligned with the access tube axis to a perpendicular alignment with minimal disturbance to the surrounding tissue is not disclosed.

The '408 publication discloses inner and outer coaxial access tubes designed to install fixed (versus polyaxial) bone anchors with the outer tube arranged to releasably engage the anchor. The placement of a fixation rod within the anchor is not addressed.

The '300 publication discloses several tools for installing a fixation rod into the rod accommodating opening in installed implants. The tools include a tubular guide extending from each implant to a location outside of the particular body with each guide having internal threads at the proximal end thereof to guide a set screw into the upper threaded portion of the implant. Each guide has a longitudinally extending slot therein for receiving the rod. A tool is disclosed for advancing the rod along each tubular guide. This arrangement would not appear to be particularly conducive to a minimally invasive procedure.

The '597 publication discloses the use of longitudinally slotted tubular extenders in which the distal ends thereof are arranged to mate with the collar of an implant. Several forms of adjuster tools are disclosed for adjusting the distance between implanted vertebrae. While installed fixation rods are disclosed the manner of inserting the rods to their final resting place within the implants is not addressed.

The '929 publication discloses a complicated tool for inserting a curved fixation rod within two or more installed implants. The tool does not appear to be particularly conducive to minimizing the disturbance of tissue around the surgical site.

It is believed that the steep learning curve required for mastering a minimally invasive approach discussed earlier is, in large part, due to the difficulties in inserting and securing the implants and fixation rods through the smaller incisions. Visualization is limited and most of the manipulation of the implants and fixation rods must occur deep within the incision. This invention addresses these difficulties by creating an improved method for the surgeon to insert the implants and deploy a fixation rod in a minimally invasive fashion, through the use of specially designed approach instrumentation and implants.

SUMMARY OF THE INVENTION

A minimally invasive implant system for immobilizing adjacent vertebral bodies, in accordance with the present invention, includes a pair of spinal implants, a fixation rod, a pair of caps for connecting the fixation rod to the implants and a pair of percutaneous tubes to enable a surgeon to secure the caps and rod to the installed implants. Each implant has a pair of elongated opposed posts extending upwardly along a longitudinal axis from a bottom support surface so that the proximal end of the posts are initially positioned outside the patient's body during the surgical procedure. The elongated posts may be formed as part of a housing which encloses the head of a pedicle screw and preferably are formed with weakened demarcation lines to enable the portions of the posts above the lines to be removed after the surgical procedure is completed. A similar housing with short posts, not designed for a minimally invasive procedure, is illustrated and described in the '291 publication. The bottom support surface may be in the form of a saddle formed in the top surface of a pressure washer arranged to lock the screw head to the housing as is shown in the '291 publication. The implants are adapted or arranged to be secured to the underlying vertebral bodies via the pedicle screws or similar devices. The posts and support surface of each implant define a transverse opening or channel for receiving a fixation or stabilizing rod. The lower portion of the posts is internally threaded to accept a locking set screw.

Each cap has a top and a bottom and opposed side wall openings adapted to extend around the posts. A locking set screw is associated with each cap so that the set screw, when rotated, will engage the internal threads on the implant posts to advance the cap along the posts toward the support surface forcing a fixation rod disposed within the transverse opening against the support surface to lock the rod and implant together. See the '291 publication.

The present invention comprises not only a pair of implants with elongated posts to allow the distal ends of the posts of each implant to be located outside of the patient's body during the surgical procedure and a cap associated with each implant as pointed out above, but a fixation rod that is pivotally mounted at one end to the bottom of one of the caps. In addition, percutaneous access tubes allow the surgeon to install the implants, caps and fixation rod in a minimally invasive manner.

The pivotally mounted cap and rod are sometimes hereinafter referred to as a cap/rod construct. This pivotal mounting arrangement eliminates the need to position a separate fixation rod into the transverse openings of the installed implants. Preferably the rod is mounted to the associated cap so that the distal or free end of the rod is maintained a given distance from the longitudinal axis of the cap as the cap and rod move down the implant posts within an access tube. This distance allows the free end of the rod to be pivoted from a position generally aligned with the longitudinal axis of one of the tube to a generally perpendicular orientation suitable for entering the transverse opening in an adjacent implant at the surgical site as will be explained.

The construction of the percutaneous access tubes and their use may be best understood in the description of the method which follows. As an initial step K wires or targeting needles may be used to locate the pedicles selected to be immobilized. Next, conventional dilators may be used to expand the incision sufficiently to receive the implants. The implants are then inserted through the respective (remaining) dilator tubes and the pedicle screws thereof are threaded into the underlying bones so that the transverse rod receiving openings or channels between the posts of the implants are aligned. Next, the pair of percutaneous access tubes are inserted over the remaining dilator tubes and the installed implants. The proximal ends of the installed implants are positioned outside of the patient's body. Alternatively, the implants may be installed through the access tubes after the dilator tubes are removed.

Both of the access tubes have rod accommodating openings extending upwardly from the distal ends thereof in at least one side. One of the tubes, designed to accommodate the cap/rod construct, is often referred to hereinafter as the first or the deployment tube. The other access tube is often referred to as the second or mating tube. The mating tube is preferably circular in cross-section and includes two aligned slots to allow the fixation rod to extend through the tube to accommodate an anticipated range of distances between adjacent vertebral bodies to be immobilized.

In one embodiment the deployment tube may have a lower circular section and an upper section with a tear drop shape in cross-section to accommodate the cap/rod construct as it moves downwardly through the implant posts. The rod accommodating opening in the deployment tube may be in the form of a vertical oriented window extending from a point in the upper section to a horizontally oriented ledge formed in the lower section and then diagonally downwardly through the lower section. The ledge serves to contact the free end of the rod and move it out of the deployment tube in a direction toward the mating tube. Rotation of the deployment tube (e.g., through say 90°) lowers the rod to the level of the bottom support surface in the transverse opening in the adjacent implant.

In another embodiment the deployment tube may comprise concentric tubes with the outer tube having a rod accommodating opening in the form of a longitudinal slot along one side thereof. The inner tube has a spiral slot extending from the distal end to about the proximal end. By rotating the slotted inner tube relative to the outer tube as the cap/rod construct moves down the implant posts, the surgeon can set the level at which the free end of the rod moves out of the concentric deployment tube and ultimately into the rod accommodating opening in the mating tube. This arrangement allows the surgeon to minimize the disturbance of the soft tissues between the installed implants.

It is to be noted that while the above summary provides an overview of the invention, it is the appended claims which define the scope thereof. The construction of the system and method for immobilizing adjacent vertebral bodies may best be understood by reference to the following description taken in conjunction with the appended drawings.

BRIEF DESCRIPTION OF THE DRAWINGS

FIGS. 1a, 1b, 1c, and 1d are a perspective, front and side elevational and a side elevational view partially in cross-section, respectively, of an implant for use in a minimally invasive spinal implant system in accordance with the present invention;

FIG. 2 is a top plan view of the implant of FIG. 1b;

FIG. 5b is an end view of the cap/rod construct of FIG. 5a;

FIGS. 5c and 5d are cross-sectional views of the cap/rod construct taken along lines 5c and 5d of FIG. 5b, respectively, showing the proximal or mounting end of the rod engaging the bottom of the cap to limit the clockwise movement of the rod as it moves downwardly along an access tube;

FIG. 5e is a side elevational view (partially in corss-section) of the cap/rod construct showing the rod fully extended in a counterclockwise direction;

FIGS. 6a, 6b and 6c are front, side elevational and top plan views, respectively, of an access deployment tube for use in securing a cap/rod subassembly to an implant;

FIGS. 7a, 7b and 7c are front, side elevational and top plan views, respectively, of an access mating tube for use in securing a cap (without an attached rod) to an implant;

DETAILED DESCRIPTION OF THE INVENTION

Figure 3:
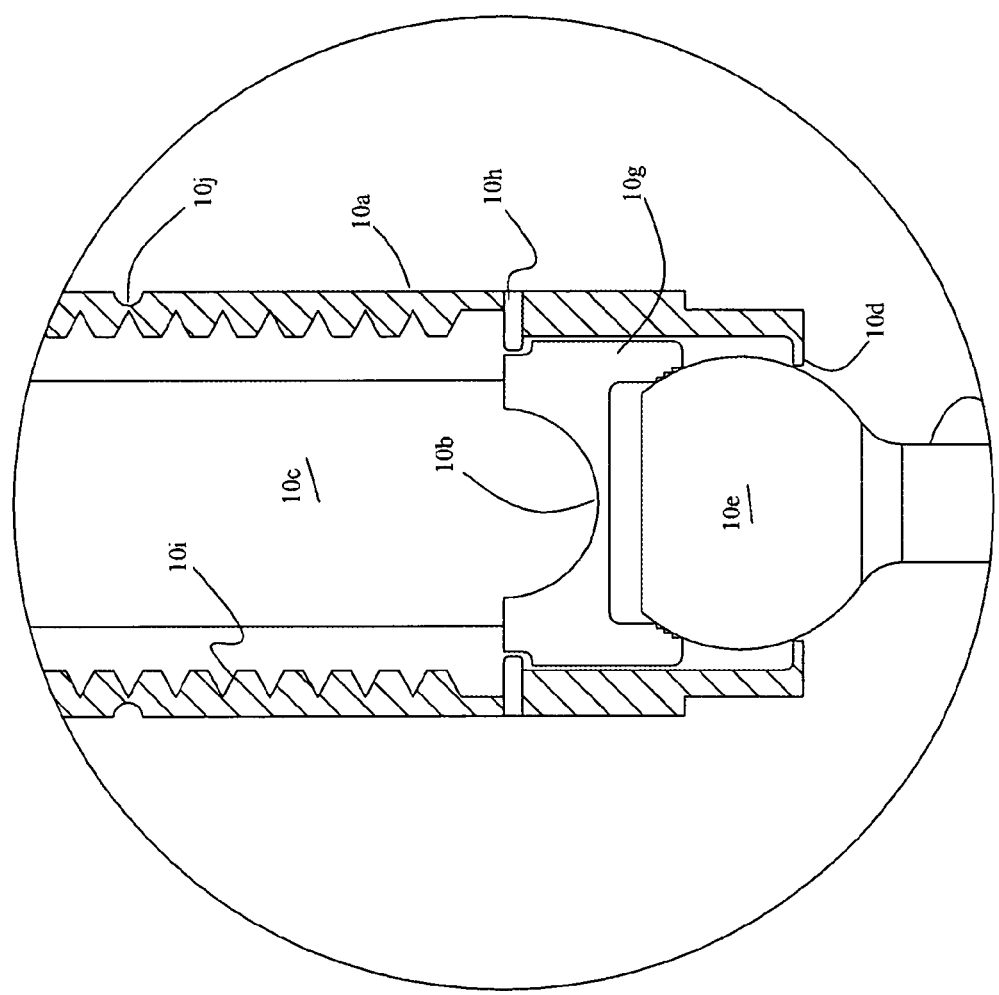
FIG. 3 is an enlarged view of the lower portion of the implant with the posts in cross-section showing the internal threads, the inwardly extending shelf which engages the bottom portion of the spherical head of the pedicle screw and the pressure washer which abuts the top of the screw and forms a saddle-shaped support surface for receiving a fixation rod.

Referring now to the drawings and particularly to FIGS. 1-3, an implant 10, for use in the present invention, has a pair of elongated posts 10a which extend upwardly along a longitudinal axis x-x from a bottom support surface 10b, generally orthogonal to the longitudinal axis. The support surface in conjunction with the posts defines a transverse opening or channel 10c. The posts are part of a housing 10m having a bottom inwardly projecting shelf 10d (FIG. 3) which engages the lower semispherical surface of the head 10e of a conventional polyaxial pedicle screw having a depending threaded shaft 10f. A pressure washer 10g, having a saddle-shaped upper surface 10b which forms the lower support surface of the implant, is held in place by pins 10h while allowing the washer to be forced downwardly against the screw head via a fixation rod and a set screw (to be described) to lock the housing and pedicle screw together. The implant housing 10m (FIG. 1c) may have a length lh within the range of about 120 mm +/−50 mm (depending on the patient's anatomy)so that the proximal end 10k (opposite the distal end 10l) extends outside of a patient's body with the implant installed in a selected vertebral body. The lower portions of the posts are internally threaded at 10i and have a weakened demarcation line at 10j (FIG. 3) to enable a surgeon to break off the portion of the posts 10a above the line once the fixation rod is secured to the installed implants as will be explained. It is to be noted that an implant, designed for traditional open incision procedure, like that shown in the '291 publication, but with slightly extended posts having a weakened demarcation line above an installed cap, has been marketed by SeaSpine under the brand name Malibu Screw System.

Figure 4B:
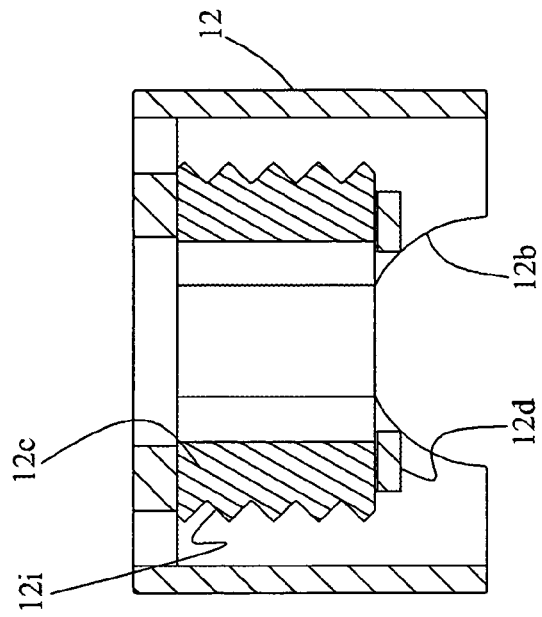
FIGS. 4a and 4b are top perspective and side cross-sectional views, respectively, of a conventional cap for use with the invention.
Figure 4A:
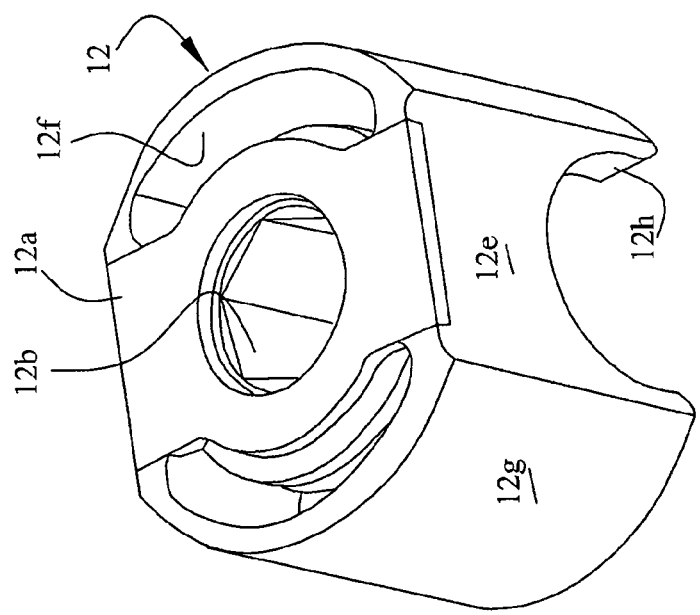
Figure 5A:
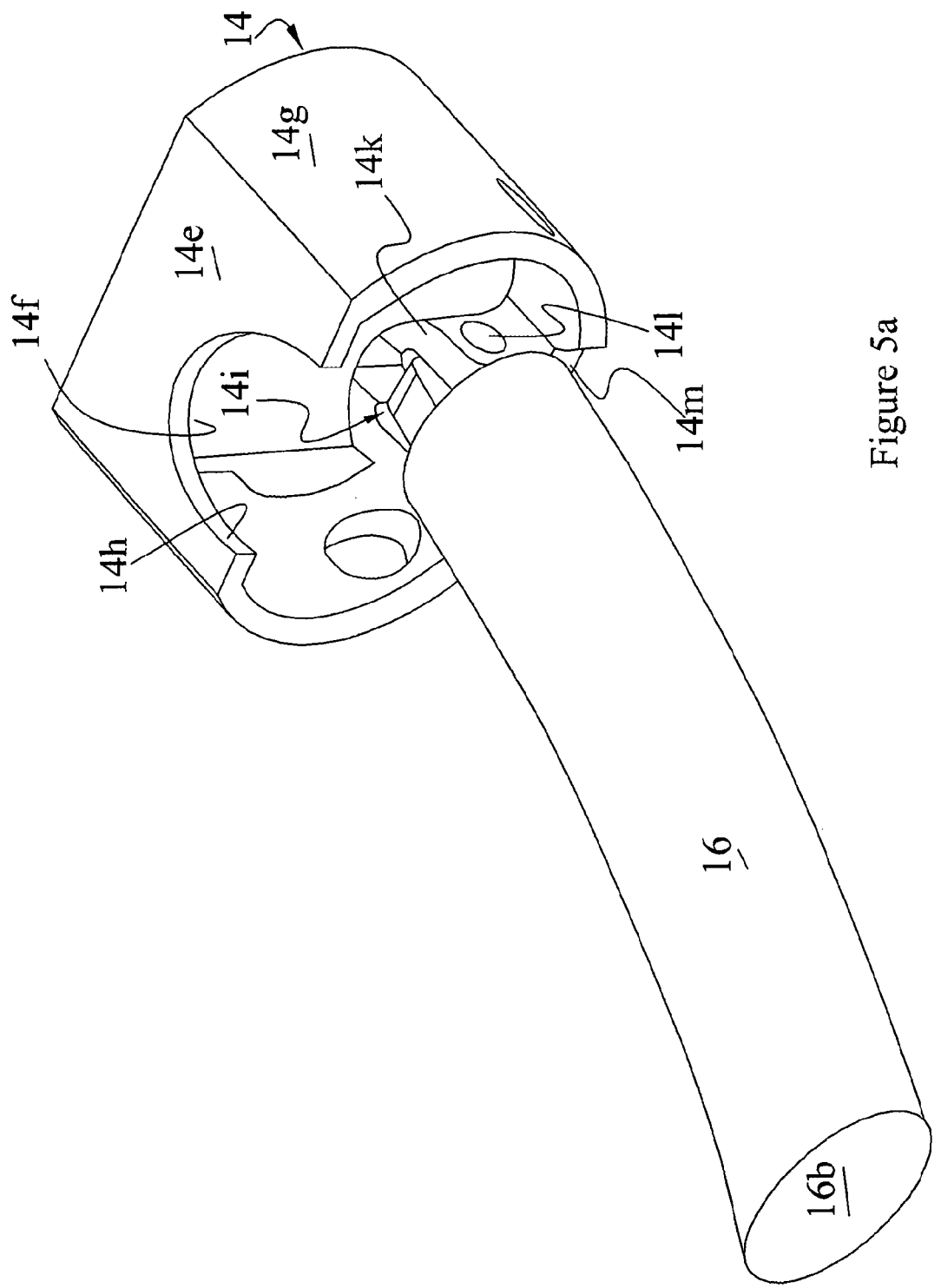
FIGS. 5a is a bottom perspective view of a modified cap with a fixation rod pivotally mounted thereto.

A cap 12, for use with the implants, is illustrated in FIGS. 4a and 4b. The cap includes top struts 12a (forming the top surface) open at the center through which a wrench, such as an alien wrench, may be inserted to engage the hexagonal wrench engaging surface 12b of a set screw 12c enclosed within the cap between the top strut, bottom strut 12d and flat end walls 12e. The cap has opposed side wall openings 12f inside of the curved side walls 12g. The cap has a bottom saddle-shaped concave surface 12h for engaging a fixation rod. The external set screw threads 12i are arranged to engage the internal threads of the implant posts to advance the cap along the posts when the set screw is rotated as is explained in more detail in the '291 publication.

A modified cap 14 with a stabilization or fixation rod 16 is coupled, e.g., mounted, to the bottom surface thereof is shown in FIGS. 5a-5d. Like components of the cap are identified with the same letter with the caveat that the bottom of the cap 14 has been reconfigured to support the proximal end 16a of the fixation rod 16. The proximal end of the rod includes a flat surface 16c with a centrally located upwardly extending semicircular tongue 16d. The tongue has a lateral bore 16e therethrough which is pivotally mounted within a clevis 14k formed in a bottom section 14i of the cap via a pin 14l (FIG. 5e). The bottom surface 14m of the clevis 14k (FIGS. 5c-5e) engages the surface 16c on the proximal end of the rod to stop the clockwise rotation of the rod (FIG. 5c) at a point within the acute angle Ø (a range of about 5° to 45°). This limitation on the rod's rotation relative to the cap's longitudinal axis 14o insures that the rod will exit the access deployment tube as it travels down the implant posts as will be explained more fully. The length of the rod will vary depending upon the number of implants and the distance between the implants to be secured to the rod. As an example, rods may have a length between as little as 30 mm and as great as 110 mm or more. I have found that a lateral distance d3 (FIG. 5c) between the rod's distal end 16b and the axis 14o within the range of about 5 to 15 mm is satisfactory for a deployment tube of the type discussed in connection with FIG. 6.

The rod can pivot in a counterclockwise direction (FIG. 5e) through an angle of up to 90° to allow the distal end 16b to extend through the rod accommodating openings in the mating tube and into the transverse opening in an adjacent implant. See FIGS. 15b-15c.

Figure 14:
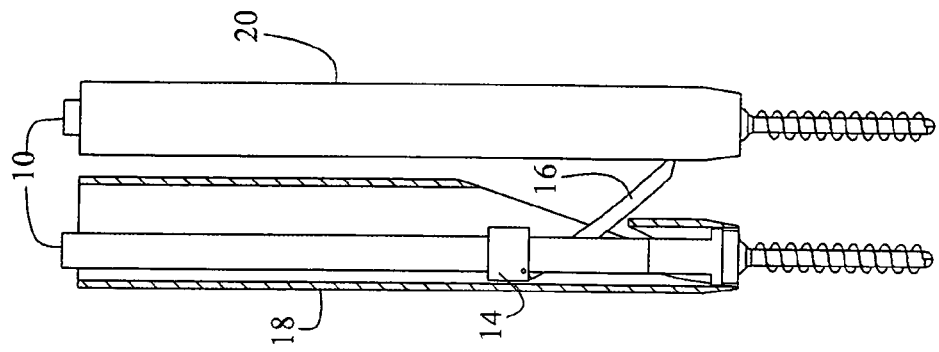
FIG. 14 is a side view, partially in cross-section, of the access tubes and implants of FIG. 10 with the cap/rod construct beginning to move down the implant posts in the access deployment tube.

The percutaneous access tubes will now be described in conjunction with FIGS. 6 and 7. The tubes have longitudinal axii 19 which are coincident with the respective longitudinal axii of the implants when positioned thereover. A percutaneous deployment tube 18 has proximal and distal ends 18a and 18b, a lower circular section 18c, and an upper section 18d as shown. The upper section has a tear drop shape, i.e., circular in cross-section through an angle λ of say 240° to 300°, and then extends outwardly about a distance $d_2$ of ½ to ¾ of the diameter $d_1$ forming an extended side 18f (FIGS. 6b and 6c) for accommodating the passage of the cap/rod construct as it travels down the implant posts as is illustrated in FIG. 14.

The deployment tube includes a rod accommodating opening 18g which extends in an expanding manner from it's apogee 18h in the upper tear drop section to a rod tip engaging ledge 18i in the lower section and then through a diagonally and downwardly extending portion 18j to the distal end 18b as is shown in FIGS. 6a and 6b. The ledge 18i serves as a kick out point to force the free or distal end 16b of the rod out of the deployment tube. The distance h from the distal end 18b to the ledge 18i is preferably within the range of 0.25-3.00 inches. As the cap/rod construct continues its downward progress along the implant posts, the rod is reoriented upwardly with respect to the tube until it becomes generally parallel to the spine, i.e., about normal to the axis 19 and extends into the rod accommodating openings in the mating tube and the transverse opening of the implant located therein. By continuing the downward movement of the rod/construct and turning the deployment tube (clockwise in FIGS. 6a-6b) through, say about 90°, the rod will be lowered to a position near the support surface in the adjacent implant. See FIGS. 14-16.

Referring now to FIGS. 7a-7c, a mating access tube 20 is circular in cross-section with proximal 20a and distal 20b ends and opposed rod accommodating openings 20c extending upwardly from the distal end sufficiently to receive the free end 16e of the rod in its fully extended position.

Figure 9:
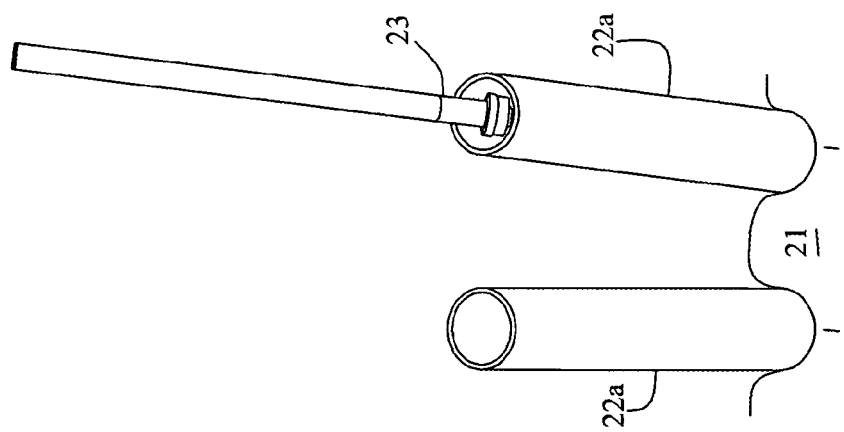
FIG. 9 is a simplified perspective view showing a portion of a tool, extending into one of the dilator tubes of FIG. 8, in the process of installing one of the implants of FIG. 1 into a vertebral body.
Figure 8:
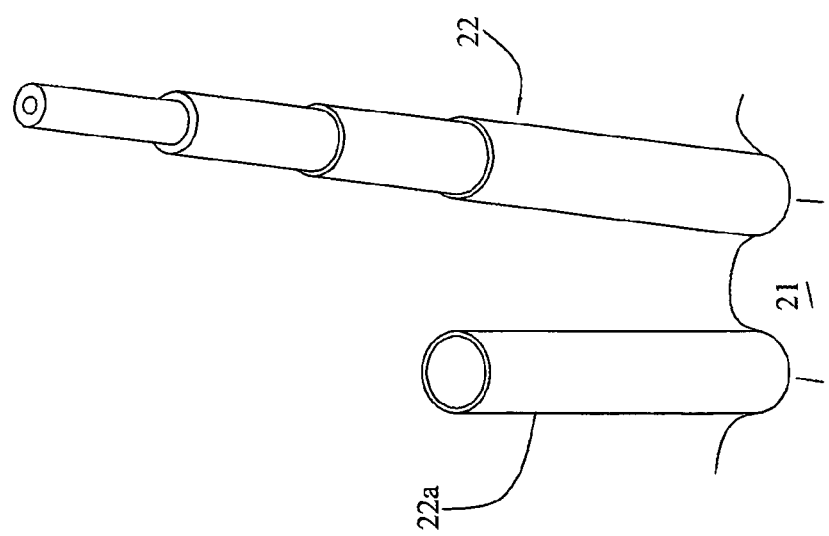
FIG. 8 is a simplified perspective view illustrating the use of a conventional dilator to expand the incision with the last dilator tube (left hand view) in place.

The method of installing the implants and cap/rod construct will now be explained in conjunction with FIGS. 8-19. Initially conventional K wires or target needles (not shown) are used to locate the targeted pedicles. Next, conventional dilators 22 are placed over the K wires (or target needles) to expand the incision to a diameter large enough to receive the implants leaving the last dilator tube 22a in place (FIGS. 8 and 9).

Next, the implants are inserted into each dilator tube and the screws thereof threaded into the respective pedicles. A tool 23 is illustrated as inserting one implant through the right hand dilator tube in FIG. 9. Next, the percutaneous tubes are placed over the dilator tubes.

Figure 10:
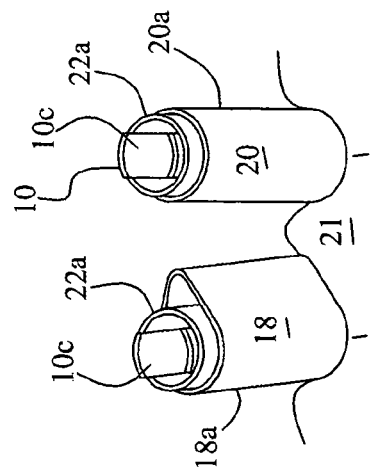
FIG. 10 is a simplified perspective view of the exposed portions (outside of a patient's body) of the access and dilator tubes and implants located therein.

FIG. 10 shows the proximal ends of installed implants and dilator and access tubes extending outside the patient's body 21 with the rod receiving transverse openings or channels 10c aligned and readily accessible to the surgeon.

Figure 11:
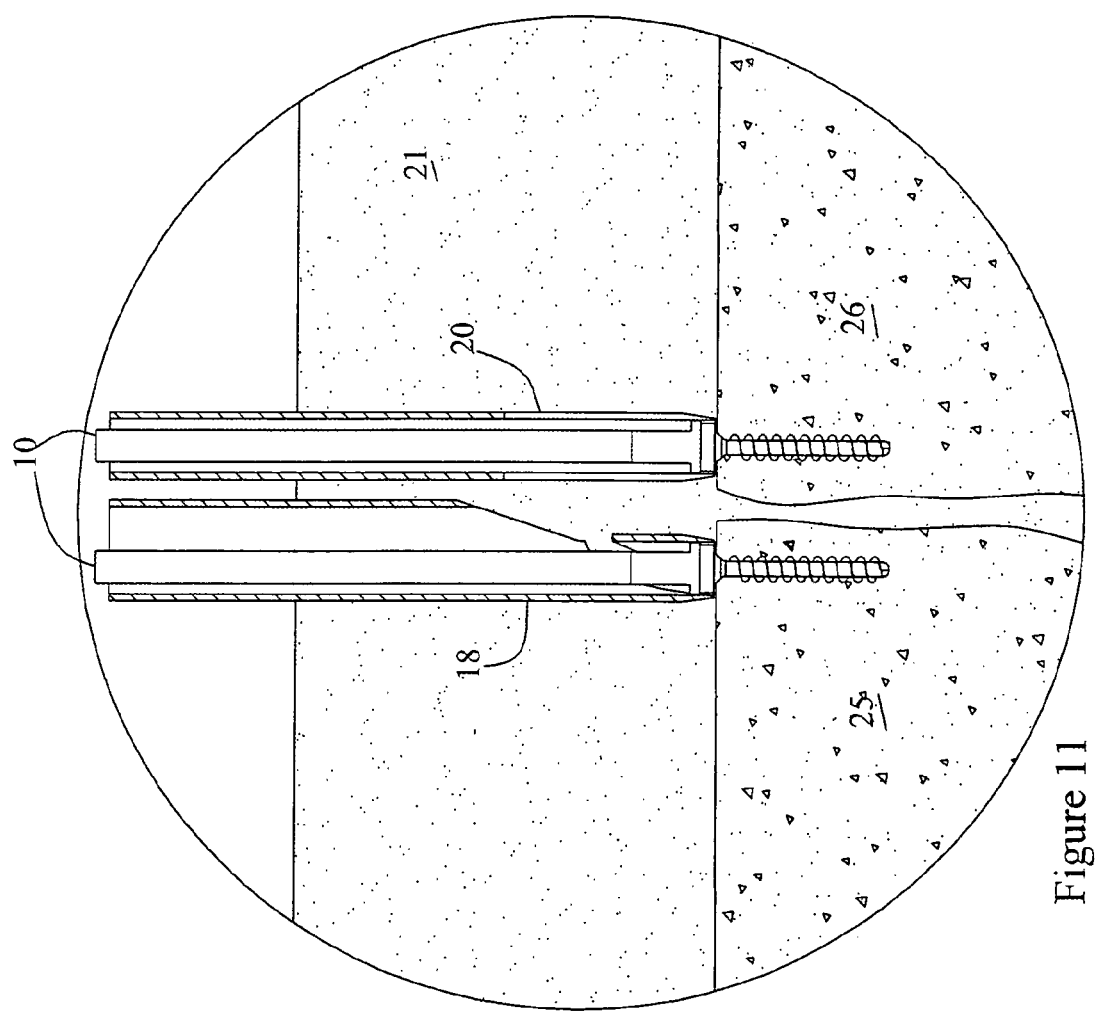
FIG. 11 is a side cross-sectional view of two implants secured to adjacent vertebral bodies within the respective access tubes, the dilator tubes having been removed.

FIG. 11 illustrates, in a side view, partially in cross-section, the implants as installed and surrounded by the deployment and mating tubes with the dilator tubes removed. Items 25 and 26 represent the vertebral bodies receiving the pedicle screws.

Figure 12:
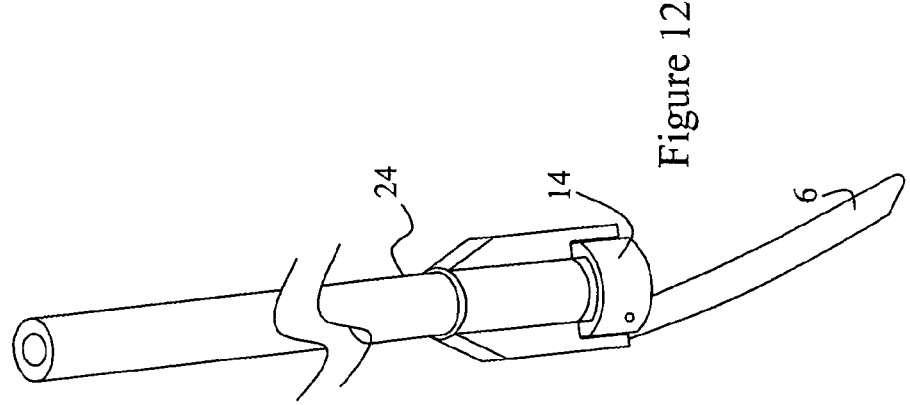
FIG. 12 is a simplified perspective view of a conventional tool grasping the end walls of a cap, with a fixation rod pivotally mounted thereon, prior to the insertion of the cap/rod assembly onto the posts of an installed implant.

FIG. 12 illustrates a tool 24 for grasping the end walls 14e of the cap 14 carrying the pivotally mounted fixation rod in preparation for inserting the cap side wall openings 14f over the posts 10a of an implant. The tool 24 includes a concentrically arranged rotatable tool (not shown), such as an allen wrench, for engaging the hexagonal cavity 14b to rotate the set screw 14c to advance the cap along the threaded portion of the posts.

Figure 13:
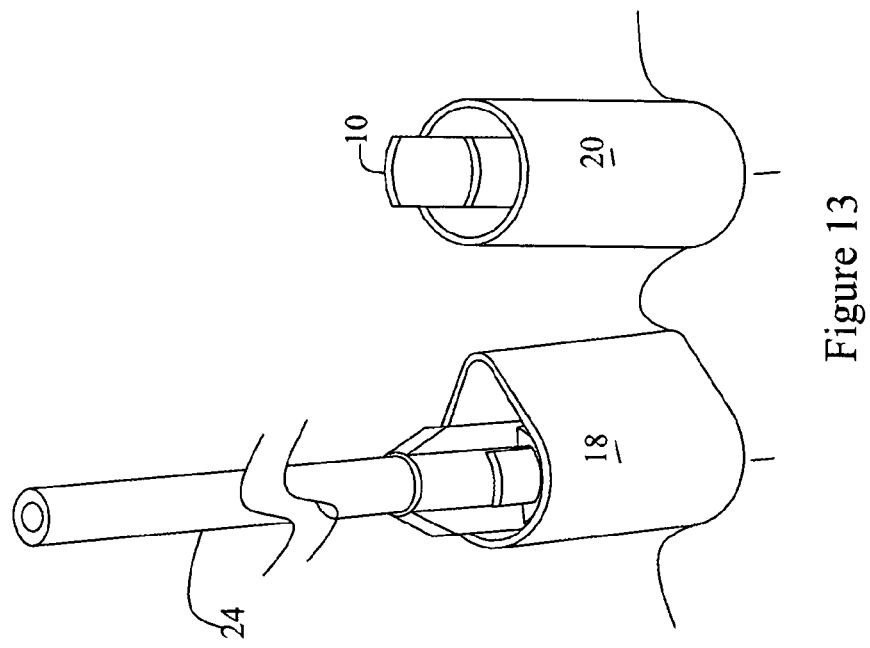
FIG. 13 is a simplified perspective view of the tool of FIG. 12 beginning to insert the cap/rod assembly of FIG. 12 in an implant.

FIG. 13 illustrates the insertion of the cap/rod construct onto the implant posts located within the proximal end of the deployment tube 18. The same tool 24 may be used to insert the cap 12 onto the posts in the implant positioned in the mating tube 20.

FIG. 14 shows the cap 14 and rod 16 proceeding downwardly along the implant posts within the deployment tube with the distal end of the rod extending into the expanded area 18f in the teardrop section of the tube.

Figure 15A:
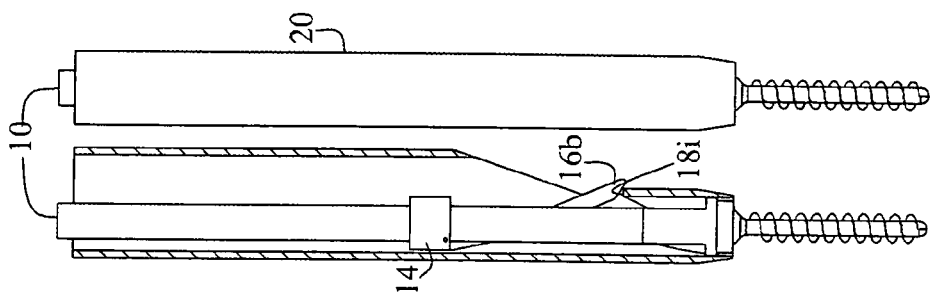
FIG. 15a is another side view of the implants and access tubes of FIG. 14 showing the cap/rod construct moved downwardly until the free end of the rod engages a lateral edge of slot formed in the lower section of the access deployment tube forcing the rod outwardly.

FIG. 15a shows the distal end 16b of the rod engaging the kick out ledge 18i in the lower section of the deployment tube.

Figure 15B:
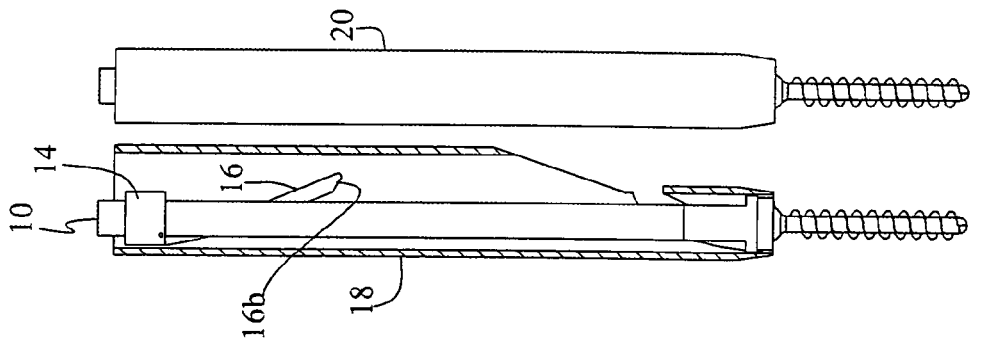
FIG. 15b is a side elevational view (partially in cross-section) of the tubes of FIG. 15a showing the fixation rod in a partially extended position.

FIG. 15b shows the rod being reoriented by the ledge as the cap 14 moves further down the implant posts.

Figure 15C:
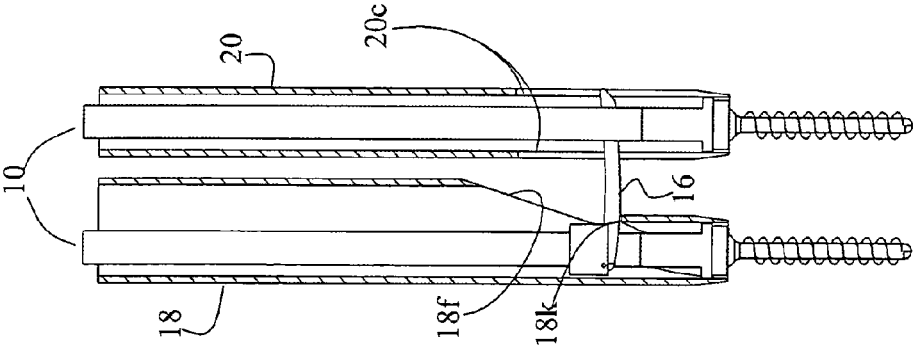
FIG. 15c is another side view of the implants and tubes of FIG. 15b with the mating tube also shown in cross-section illustrating the fixation rod in a fully extended position, reoriented and positioned within the rod accommodating openings in the mating tube and the transverse opening or channel in the adjacent implant.

FIG. 15c shows the cap/rod construct advanced along the implant posts in the deployment tube to reorient the rod at a right angle to the tube's longitudinal axis with the rod extending through the two rod accommodating openings 20c in the mating tube and the transverse opening 10c in the implant positioned in the mating tube.

Figure 17:
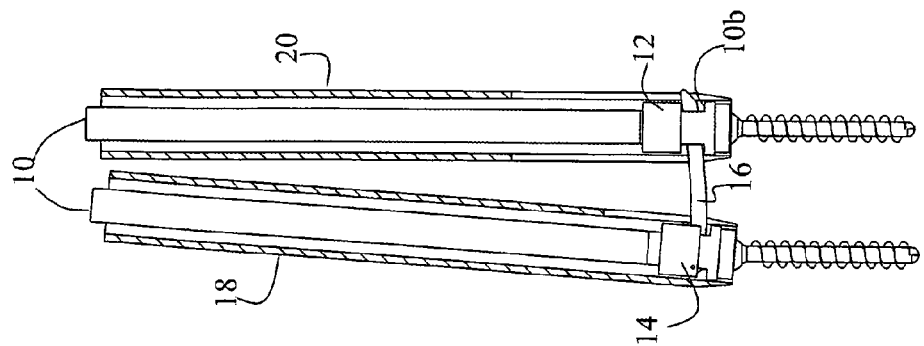
FIG. 17 is another side view of the implants and access tubes with the cap in the adjacent implant about to be fully seated.
Figure 16:
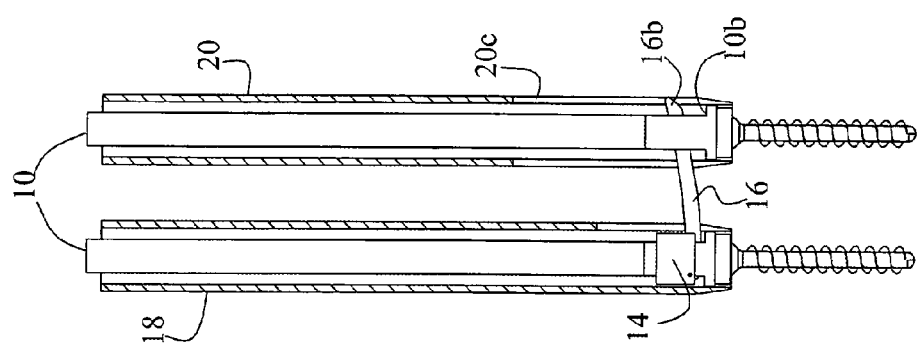
FIG. 16 is another side view of the implants and access tubes showing the cap fully seated in the implant located in the deployment tube and the distal end of the rod positioned near the support surface in the adjacent implant.

FIG. 16 shows the deployment tube rotated, say through 90°, as the cap is lowered to its final position. This lowers the rod so that it is positioned slightly above the support surface 10b in the adjacent implant. The cap 14 is also shown in its locked position. FIG. 17 shows the cap 12 extending down the posts in the adjacent implant, but not in a fully locked positioned.

Figure 19:
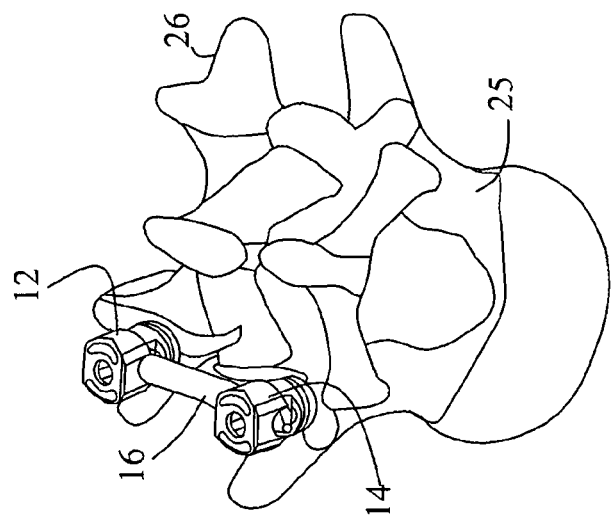
FIG. 19 is a perspective view of the implants of FIG. 18 with the upper portions of the implant posts above the demarcation lines removed.
Figure 18:
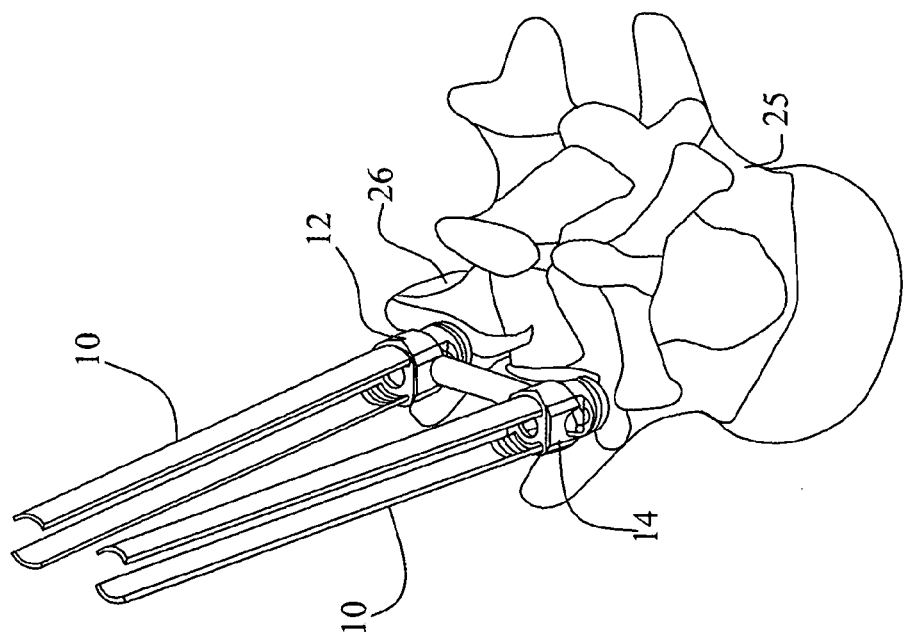
FIG. 18 is a perspective view of the implants of FIG. 17 installed in simulated vertebrae with both caps fully seated and the access tubes removed.

FIG. 18 shows the implants installed in simulated adjacent vertebral bodies 25 and 26 with both caps in a locked position and the access tubes removed. FIG. 19 is the same view as FIG. 18 with the portions of the posts above the demarcation lines 10j broken off and removed.

It is to be noted that while the drawings illustrate only one side of the spine as receiving the implants, locking caps and stabilizing rods, the system and method is equally applicable for treating the opposite side of the spine. In addition the length of the pivotally mounted fixation rod is not limited to that required to span only the length between two implants. More than two implants may be locked to a single rod.

Figure 20B:
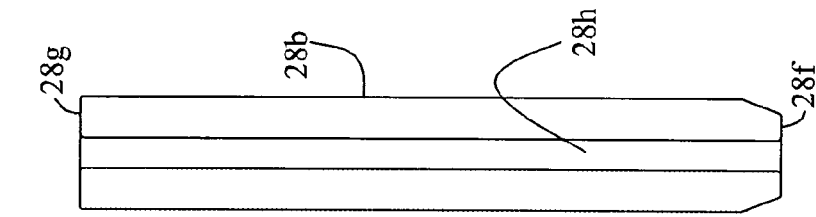
FIGS. 20a and 20b are side elevational views of an alternative access deployment tube arrangement for use in securing a cap/rod subassembly to an implant.
Figure 20A:
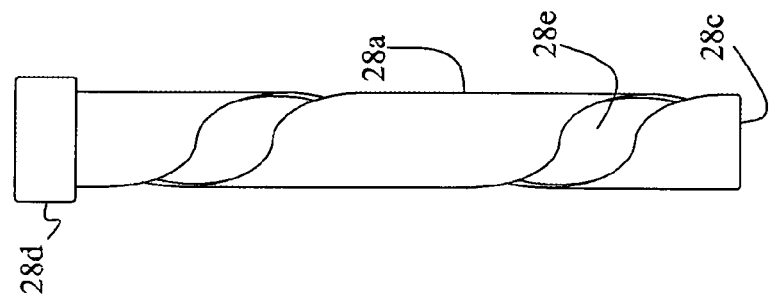

FIGS. 20a and 20b are side elevational views of an alternative embodiment of a deployment tube comprising elongated inner and outer tubes 28a and 28b, respectively. The inner tube 28a extends from a distal end 28c to a proximal end formed by collar 28d. The inner tube includes a spiral slot 28e extending upwardly from the distal end to the collar. The outer tube also extends from a distal (28f) to a proximal (28g) end and is provided with a longitudinally extending rod accommodating slot or opening 28h along one side.

Figure 21:
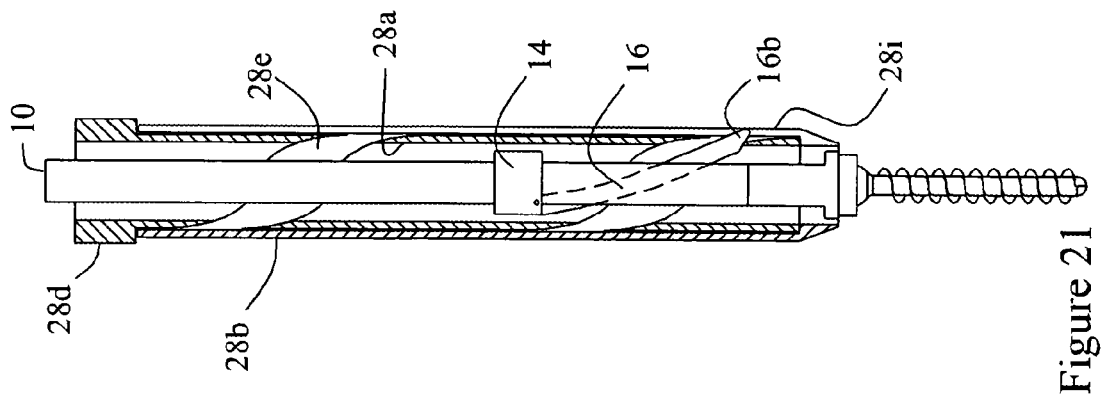
FIG. 21 is a side elevational view (partially in cross-section) of the tubes of FIGS. 20a and 20b positioned over an installed implant with a cap/rod subassembly lowered into the implant so that the free end of the rod is engaging an edge of the spiral slot beginning to force the rod outwardly of the deployment tube.

FIG. 21 is a side view, partially in cross-section, showing the tubes in a nested condition surrounding an implant. By manipulating the inner tube 28a while the cap/rod construct 14/16 travels down the two tubes the surgeon can set the point at which the rod 16 emerges from the deployment tube. The rod free end 16b will remain inside of the deployment tube until the rod free end is aligned with the slots 28e and 28h, at which point the rod starts exiting the tube. The edge of the spiral slot contacting the rod will reorient the rod into an angle paralleling the spine. FIG. 21 shows the free end of the rod engaging an edge 28i of the spiral.

There has thus been described a novel system and method for immobilizing adjacent vertebral bodies with minimal disturbance of the muscle and soft tissue surrounding the targeted vertebrae. Modifications and perhaps improvements to the system and method may occur to those skilled in the art without involving a departure of the spirit and scope of the present invention as defined by the appended claims.

What is claimed is:

1. In a minimally invasive implant system for use in immobilizing vertebral bodies, the combination comprising:
a pair of implants, adapted to be secured to adjacent vertebral bodies, each implant having a pair of elongated posts extending upwardly along a longitudinal axis from a bottom support surface, the posts and the bottom support surface defining a transverse opening for receiving a stabilizing rod, at least a portion of the posts having internal threads;
a pair of caps, wherein each cap comprises a top strut and a bottom strut and an external member connecting the top strut and the bottom strut, wherein the external member has an inside contour permitting passage therethrough of the posts, and wherein the top strut has an upper pair of openings therethrough permitting passage therethrough of said posts, and the bottom strut has a lower pair of openings therethrough permitting passage therethrough of said posts, each cap having an externally threaded set screw located between the top strut and the bottom strut and located interiorly with respect to the external member, wherein the top strut prevents passage of the set screw past the top strut, wherein the bottom strut prevents passage of the set screw past the bottom strut, and wherein the external member prevents passage of the set screw from the interior of the external member to the exterior of the external member, the set screw being free to rotate with respect to the cap, the externally threaded set screw external threads being dimensioned to engage the implant internal threads, whereby rotation of the set screws will advance the caps along the threaded portion of the implant posts toward the support surface; and
a fixation rod having proximal and distal ends, the proximal end being pivotally mounted on one of the caps, wherein the fixation rod remains mounted on the one cap during and after implantation.

2. The implant system of claim 1 wherein the posts have proximal and distal ends and a length l sufficient for the proximal ends to extend outside of a patient's body with the implants installed in the selected vertebral bodies.

3. The implant system of claim 2 further including first and second access tubes, each tube having a longitudinal axis and being arranged to receive one of the implants and associated caps.

4. The implant system of claim 3 wherein each of the tubes has a proximal and distal end and defines at least one fixation rod accommodating opening extending upwardly from a point adjacent the distal end thereof.

5. The implant system of claim 4 wherein the first access tube includes means for pivoting the rod carried by said one cap outwardly through the rod accommodating opening in said tube and into the rod accommodating opening of the second tube and the transverse opening in the other implant as the cap moves downwardly along the first access tube.

6. The implant system of claim 5 wherein the first access tube has an upper and a lower section with the sections having a tear drop shape and a circular shape in cross-section, respectively, the rod accommodating opening being formed in both sections.

7. The implant system of claim 5 wherein the rod accommodating opening in the first access tube is in the form of a window extending through the distal portion of the tear drop section to a lateral edge in the second section and then along a diagonal path to about the distal end of the tube, the lateral edge being arranged to engage the distal end of the rod as it moves downwardly along the post and change the rod's orientation as it exits the opening.

8. The implant system of claim 5 wherein each cap has a longitudinal axis and wherein the mounting between the cap and the rod maintains a minimum preset distance d3 between the rod and the longitudinal axis of the cap as the cap moves downwardly along the posts so that the rod will engage the lateral edge of the first access tube.

9. The implant system of claim 5 wherein the first access tube comprises two concentric tubes with the outer tube defining the rod accommodating opening and the inner tube being rotatable within the outer tube, the inner tube having a spiral groove therein, the groove and distal end of the rod, when aligned with the rod accommodating opening in the outer tube, serving to cause the distal end of the rod to pivot upwardly and its extends through the opening.

10. The implant system of claim 7 wherein the rod accommodating openings in the outer access tube is in the form of at least one longitudinal slot.

11. The implant system of claim 7 wherein a distance d3 is defined as a lateral between the distal end of the rod and a centerline axis of the tube, and d3 is within the range of about 5 to 15 mm.

12. The implant system of claim 1 further including a pivot connection between the cap and the rod.

13. The implant system of claim 12 wherein the pivot connection includes the cap having a clevis and the rod proximal end having a tongue pivotally engaging the cap clevis.

14. The implant system of claim 12 wherein the pivot connection further includes a pin connecting the cap and rod.

15. A minimally invasive method for immobilizing spinal segments comprising:
  a) providing first and second implants adapted to be secured to adjacent segments, each implant having a pair of elongated posts extending upwardly from a bottom support surface, the posts and support surface defining a transverse opening for receiving a fixation rod, at least a portion of the posts having internal threads;
  b) providing first and second caps, each cap having a top strut and a bottom strut and an external member connecting the top strut and the bottom sturt, wherein the external member has an inside contour permitting passage therethrough of the posts, and wherein the top strut has an upper pair of openings therethrough permitting passage therethrough of said posts, and the bottom strut has a lower pair of openings therethrough permitting passage therethrough of said posts, each cap having an externally threaded set screw located between the top strut and the bottom strut and located interiorly with respect to the external member, wherein the top strut prevents passage of the set screw from the bottom strut, and wherein the external member prevents passage of the set screw from the interior of the external member to the exterior of the external member, the set screw being free to rotate with respect to the cap and threadably engaging the posts so as to advance the cap along the threaded porton of the posts of a respective implant, the first cap having a fixation rod pivotally coupled at one end to the first cap;
  c) providing first and second elongated percutaneous access tubes aligned along imaginary longitudinal axes and having proximal and distal ends, each of the tubes having at least one rod accommodating opening extending upwardly from adjacent the distal end thereof for accommodating the passage of the rod therethrough;
  d) installing the first and second implants into respective spinal segments with the transverse openings thereof in alignment;
  e) positioning the first and second access tubes over the implants before or after the implants are installed;
  f) progressively moving the first cap along the posts of the first implant while pivoting a free end of the rod through the rod accommodating openings in the first and second tubes and into the rod receiving opening in the second implant; and
  g) securing the first and second caps over the rod to lock the rod to the implants.

16. The method of claim 15 further including removing the access tubes.

17. The method of claim 15 wherein the implant posts have a weakened demarcation line adjacent the top of the installed caps and further including severing the posts at the demarcation lines and removing the portions thereof extending above the lines.

18. The method of claim 15 wherein the rod is pivotally mounted to a bottom of the first cap.

19. The method of claim 15 wherein the first access tube comprises an inner and an outer tube with the inner tube having a spiral slot therein and the outer tube having a longitudinally extending slot on one side forming the rod accommodating opening and wherein the step of moving the first cap along the first implant posts includes the sub-step of rotating the inner tube to align the spiral slot with the rod accommodating opening to allow the free end of the rod to exit the first access tube.

20. The method of claim 15 wherein the step of moving the first cap along the first implant posts includes pivoting the rod through an angle of about 90° to the longitudinal axis of the first tube as it extends through the rod accommodating openings and then rotating the first tube lowering the rod to a position adjacent the support surface in the second implant.

21. The method of claim 15 further including pivoting the rod relative to the cap about a pivoting axis of the cap.

22. A implant system for use in a minimally invasive surgical procedure to immobilize adjacent vertebral bodies, the system having (1) a pair of implants adapted to be secured to respective vertebral bodies with each implant having a pair of posts extending upwardly from a bottom support surface defining a transverse opening for receiving a stabilizing rod, (2) a stabilizing rod, and (3) a pair of caps having a top strut and bottom strut and an external member connecting the top strut and the bottom strut, wherein the external member has an inside contour permitting passage therethrough of the posts, and wherein the top strut has an upper pair of openings therethrough permitting passage therethrough of said posts, and the bottom strut has a lower pair of openings therethrough permitting passage of said posts, the cap having an externally threaded set screw located between the top strut and the bottom strut and located interiorly with respect to the external member, wherein the top strut prevents passage of the set screw past the top strut, wherein the bottom strut prevents passage of the set screw past the bottom strut, and wherein the external member prevents passage of the set screw from the interior of the external member to the exterior of the external member, the set screw being free to rotate with respect to the cap and threadably engaging the associated posts so as to advance the caps along the posts to capture the stabilizing rod between the caps and the implant support surfaces; and
  characterized by the stabilization rod being nonreleaseably pivotally carried on one of the caps.

23. The implant system of claim 22 wherein the rod is pivotally carried on one of the caps in a first position and is rotatable to a second position relative to the cap about a hinge.

24. The implant system of claim 23 wherein the cap includes a saddle opposite the hinge receiving a portion of the rod opposite the hinge when in the second position.

25. In a spinal implant system for use in immobilizing vertebral bodies in a minimally invasive manner, the combination comprising:
  a pair of implants having proximal and distal ends and lengths l sufficient so that the proximal ends of the implants extend outside of a patient's body when the implants are installed, each implant having a pair of opposed elongated posts which in conjunction with an orthogonally arranged support surface define a transverse opening for receiving a stabilizing rod;
  a fixation rod having proximal and distal ends; and
  a cap having a top strut and a bottom strut and an external member connecting the top strut and the bottom strut, wherein the external member has an inside contour permitting passage therethrough of the posts, and wherein the top strut has an upper pair of openings therethrough permitting passage therethrough of said posts, and the bottom strut has a lower pair of openings therethrough permitting passage therethrough of said posts, the cap having an externally threaded set screw located between the top strut and the bottom strut and located interiorly with respect to the external member, wherein the top strut prevents passage of the set screw past the top strut, wherein the bottom strut prevents passage of the set screw past the bottom strut, and wherein the external member prevents passage of the set screw from the interior of the external member to the exterior of the external member, the set screw being free to rotate with respect to the cap and threadably engaging the associated posts so as to advance the cap along the posts toward the support surface to lock a stabilizing rod therebetween, the proximal end of the rod being nonreleaseably pivotally coupled to one of the caps so that the rod when pivoted will extend between the transverse openings in adjacently installed implants.

26. The system of claim 25 wherein the implant posts have a weakened demarcation line above the upper surface of an installed cap so that the portions of the posts above the demarcation lines can be broken off and removed.

27. The system of claim 25 wherein one of the caps is connected to the rod proximal end by a hinge, the rod being pivotal about the hinge between a first angle and a second angle.

* * * * *